United States Patent [19]

Zehner

[11] 4,005,131
[45] Jan. 25, 1977

[54] SYNTHESIS OF OXALATE ESTERS FROM CARBON MONOXIDE AND ACETALS OR KETALS

[75] Inventor: Lee R. Zehner, Media, Pa.

[73] Assignee: Atlantic Richfield Company, Los Angeles, Calif.

[22] Filed: Jan. 2, 1976

[21] Appl. No.: 646,118

[52] U.S. Cl. .................. 260/485 R; 260/465 D; 260/465.4; 260/485 H; 260/485 J; 260/485 L; 260/485 P

[51] Int. Cl.² .................................... C07C 69/36

[58] Field of Search ....... 260/485 R, 485 L, 485 H, 260/485 J, 485 P, 465 D, 465.4

[56] References Cited

UNITED STATES PATENTS 3,393,136  7/1968  Fenton et al. .............. 260/485 R

FOREIGN PATENTS OR APPLICATIONS 2,213,435  10/1973  Germany .............. 260/485 R Primary Examiner—Jane S. Myers
Attorney, Agent, or Firm—Delbert E. McCaslin

[57] ABSTRACT

A process for the preparation of oxalate esters by the catalytic oxidative carbonylation of acetals and ketals with carbon monoxide and oxygen-containing gas in the presence of a metal salt catalyst, an amine base and a catalytic amount of an alcohol. Preferably a catalytic amount of particular metal oxidizing salts is employed along with a catalytic amount of an acid or an amine salt compound. Alternatively various counterions and ligands of the metal salt catalysts may be employed.

25 Claims, No Drawings

4,005,131

SYNTHESIS OF OXALATE ESTERS FROM CARBON MONOXIDE AND ACETALS OR KETALS

BACKGROUND OF THE INVENTION

A number of prior art processes have been proposed for the preparation of oxalate esters by the oxidative carbonylation of alcohols in the presence of metal salt catalysts, dehydrating agents and ferric or cupric redox agents in solution.

The present invention is directed to a process for the preparation of oxalate esters in high yield and avoiding the problems associated with the prior art processes of carbonylating alcohols to obtain the desired oxalate ester. More particularly, the present process relates to the synthesis of oxalates by reacting carbon monoxide and oxygen with an acetal or a ketal under elevated temperature and pressure conditions in the presence of a catalytic amount of a palladium, platinum, cadmium, cobalt, rhodium, zinc or copper salt catalyst and at least a catalytic amount of an amine base and a catalytic amount of an alcohol and includes the employment of catalytic amounts of copper (II) or iron (III) oxidant salts in addition to catalytic amounts of an ammonium or substituted ammonium salt compound and ligands of the metal salt catalysts.

U.S. Pat. No. 3,393,136 describes a process for the preparation of oxalates by contracting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liquid phase to prevent the accumulation of water.

In a recent article by Donald M. Fenton and Paul J. Steinwand, Journal of Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalates are not produced. The necessity of the iron or copper redox system during the oxalate synthesis is emphasized.

A recent West German Pat. No. 2,213,435 discloses a method for the synthesis of oxalic acid and oxalate esters in water and alcohol respectively. A platinum group metal salt, a salt of a metal more electropositive than the platinum group metal, e.g. copper (II) chloride and an alkali metal salt comprise the catalyst. Oxygen in stoichiometric amounts was employed as the oxidant. A disadvantage of such reaction is that explosive mixtures of oxygen and carbon monoxide are necessary to effect reaction. Under non-explosive conditions only trace amounts of oxalate can be obtained.

Many important commerical applications have been developed for the oxalate products of this invention, for example, as cellulose ether or ester and resin solvents, as dye intermediates and the preparation of pharmaceuticals.

The process of the invention provides a method of carrying out the oxidative carbonylation of an acetal or ketal to produce an oxalate ester without the coproduction of water which acts to poison the catalyst system and which even in small amounts also causes the production of large quantities of carbon dioxide and an attendant loss of the desired oxalate ester. Thus, by the process of the present invention, only very small concentrations of water can accumulate in the reaction system since by the mechanism of the reaction any water which might be formed is rapidly consumed upon formation of coproduct aldehyde or ketone. In addition, the coproduction of carbonate esters associated with such carbonylation reactions are minimized giving excellent selectivities to oxalate esters with high conversions of the acetal or ketal. The aldehyde or ketone produced by the oxidative carbonylation reaction of the acetal or ketal respectively may be readily separated from the desired oxalate and converted back to the respective reactant.

Other advantages of the present invention, as compared to known prior art processes for the production of oxalates are (1) elimination of hazardous operational conditions by avoiding explosive mixtures of oxygen and carbon monoxide, (2) avoiding the use of large amounts of corrosive chloride ions (3) ease of recovery and regeneration of the metal salt catalysts for reuse in the process and (4) the ability to employ in the process as catalysts the more readily available copper salts and other metal salts in place of the more expensive platinum group metal salts.

SUMMARY OF THE INVENTION

According to the present invention there is provided a much improved catalytic oxidative carbonylation process for the preparation in high yield of oxalate esters by reacting stoichiometric quantities of carbon monoxide and oxygen with an acetal or ketal, which process is carried out at elevated temperatures and pressures in the presence of a metal salt catalysts and a catalytic amount of an amine base and an alcohol and under relatively anhydrous conditions. The process of the invention also preferably employs, in catalytic amounts, particular metal oxidant salts and an acid or an ammonium or substituted ammonium salt compounds to provide a pronounced effect on oxalate ester selectivity, and high conversions to the oxalates over the carbonates which may be present in only trace amounts. In addition, it has been found that alternatively catalytic amounts of various ligands, which will not work in themselves, may be used as co-catalysts in conjunction with the metal salt catalysts, the amines, the amine salts and the oxidant salts.

It is a primary object of this invention to provide a process for the preparation of oxalate esters in high yield while avoiding operational problems associated with prior processes.

It is another object of this invention to provide a novel reaction system useful in the conversion of carbon monoxide, oxygen and acetals or ketals to oxalate esters.

It is a further object of this invention to provide a specific mechanism for the employment of catalysts, oxidant salts, amines salts and amines in an oxidative carbonylation process employing acetal or ketal reactants.

These and other objects and advantages of this invention will become apparent from the description of the invention which follows and from the claims.

DESCRIPTION OF THE INVENTION

In accordance with the invention, an oxalate ester is produced by reacting, under relatively anhydrous liquid phase conditions, an acetal or ketal with carbon monoxide and oxygen at elevated temperatures and pressures in the presence of a catalyst comprising a palladium, rhodium, platinum, copper, cobalt, cadmium or zinc metal salts, with or without a ligand such as lithium iodide as a co-catalyst, and in catalytic amounts, ammonia or a primary, secondary or tertiary amine and an alcohol and preferably in catalytic amounts also a copper (II) or iron (III) metal oxidant salt, an ammonium salt or amine salt or acid stronger than water which will not complex too strongly with the metal salt catalyst. The synthesis of the oxalate esters in carried out according to the following postulated equations:

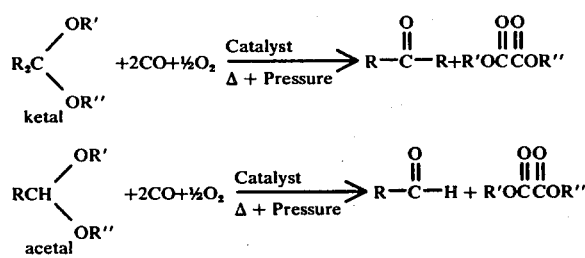

wherein R is an alkyl, alicyclic or aryl group and R' and R'' are substituted or unsubstituted alkyl or aralkyl groups. R' and R'' may be the same or different and may contain other substituents such as amido, alkoxy, amino, carboxy, cyano, etc. radicals. The substituents, in general, do not interfere with the reaction of the invention.

As indicated above, catalytic amounts of an amine, and an alcohol are added to the reaction mixture and preferably in addition in catalytic amounts a metal oxidant salt and an amine salt. The amine salt so added may also be formed in situ in the reaction mixture by the addition of an acid such as sulfuric acid in order to form the necessary quantity of amine salt. Thus, for example, triethylamine can be employed initially in sufficient amounts and sulfuric acid added to form triethylammonium sulfate in the desired catalytic quantities. The addition of the amine salt maintains the proton acidity of the reaction system.

The reaction between the acetal or ketal, carbon monoxide and oxygen may be carried out in an autoclave or any other high pressure reactor. A general procedure is to charge the acetal or ketal, amine, amine salt (or the required amount of amine and acid), catalyst, and the oxidant salt into the reaction vessel, introduce the proper amount of carbon monoxide and oxygen to the desired reaction pressure and then heat the mixture to the desired temperature for the appropriate period. The reaction can be carried out batchwise or as a continuous process and the other of addition of the reactants may be varied to suit the particular apparatus employed. The reaction products are recovered and treated by any conventional method such as distillation and/or filtration, etc. to effect separation of the oxalate from unreacted materials, catalyst, oxidant salt, amine salt, by products, etc.

The acetals and ketals employed in stoichiometric quantities and suitable for use in the process of the present invention conform to the general formulae

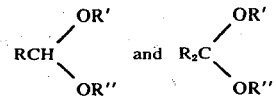

respectively as indicated hereinabove. R may be an alkyl group containing from 1 to 20 carbon atoms preferably 1 to 10 carbon atoms. R may also be an alicyclic, or an aryl group containing one or more benzenoid rings preferably not more than 3 rings which may be fused or joined by single valency bonds. R' and R'' which may be the same or different may be substituted or unsubstituted alkyl or aralkyl groups preferably containing from 1 to 10 carbon atoms in the alkyl chain and from 1 to 2 aryl group substituents when R' or R'' or both is an aralkyl group. In the preparation of oxalate esters by the present process the ketals are preferred over the acetals due to possible side reactions such as peroxidation. Generally in the instant process the acetals react slower than the ketals.

Repesentative acetals suitable for use in this invention include, for example, the 1,1-dialkoxyalkanes such as dimethoxymethane, dibutoxymethane, 1,1-dimethoxyethane, 1,1-dimethoxypropane, etc. as well as, for example 1-methoxy-, 1-ethoxy- and 1-propoxy-tetrahydrofuran, 2,5-dimethoxy-2,5-dihydrofuran, 2,5-diethoxy-tetrahydrofuran, ethyl diethoxyacetate, 1,1,2-trimethoxyethane, 1,1-dimethoxy-2-propene, 2-ethoxy-4-methyl-3,4-dihydro-2H-pyran and dimethoxy- and diethoxy-phenylmethane, etc.

Representative ketals suitable for use in this invention include for example, 2,2-dimethoxy-, 2,2-diethoxy-, and 2,2-dipropoxy-propane, butane, pentane, etc., 2,2-dimethoxy- and 2,2-diethoxy-1-pentene, 1-butene, etc., 1,1-dimethoxycyclohexane, 1,1-diethoxycyclohexane, 1,1-dibutoxycyclohexane, etc., 1,1-dibutoxy-4-methylcyclohexane, 1,1-dimethoxy-1,2,3,4-tetrahydronaphthalene, etc. and 1,1-bis(2-propenoxy)cyclohexane.

The alcohols employed in catalytic quantities and suitable for use in the process of the present invention can be monohydric saturated aliphatic and alicyclic alcohols or aromatic alcohols and may contain other substituents such as amido, alkoxy, amino, carboxy, cyano, etc. radicals in addition to the hydroxyl group. The substituents, in general, do not interfere with the reaction of the invention.

The alcohols which may be employed in concentrations of from 0.1 to 50 weight percent preferably from 1 to 3 weight percent and which may be primary, secondary or tertiary alcohols conform to the general formula ROH, wherein R is an optionally substituted aliphatic or alicyclic group preferably containing from 1 to 20 carbon atoms. R May be an aromatic group containing one or more benzenoid rings preferably not more than 3 rings which may be fused or joined by single valency bonds, directly or through bridging groups which may be, for example, oxygen or sulfur atoms or sulfoxide sulfone or carbonyl groups or alkylene groups in which, if desired, the carbon chain may be interrupted by, for example, oxygen or sulfur atoms, sulfoxide, sulfone or carbonyl groups, for example methylene, oxymethylene, dimethylene sulfone or dimethylene ketone groups. Representative alcohols especially suitable for use in this invention are monohydric alcohols such as methyl, ethyl, n-, iso-, sec-, and tert-butyl, amyl, octyl, lauryl, n- and iso-propyl, cetyl, benzyl, chlorobenzyl and methoxybenzyl alcohols as well as, for example cyclohexanol, octanols, heptanols, decanols, undecanols, 2-ethyl hexanol, nonanol, myristyl alcohol, stearyl alcohol, methyl cyclohexanol, oleyl and eicosonyl alcohols, and the like. The preferred alcohols are the primary and secondary monohydric alcohols, such as methanol, ethanol and 2-propanol.

The amines employed in catalytic quantities in the process of the invention which may be ammonia or primary, secondary or tertiary amines include aliphatic, cycloaliphatic, aromatic and heterocyclic amines or mixtures thereof. The amines may be unsubstituted or contain other substituents such as halides, alkyl, aryl, hydroxy, amino, alkylamino, carboxy, etc. The amines may be employed in the reaction in concentrations of from 0.1 to 5 weight percent and preferably at a concentration ~3 weight percent.

Representative amines, as hereinabove described, include for example, mono-, di- and tri-methyl, ethyl and propyl amines, iso- and diisopropylamines, allyl amines, mono-, di-, tri-, iso and diisobutyl amines, 1-methyl propyl amine, 1,1-dimethylethyl amine, amyl amines, cyclohexyl amine, dicyclohexylamine, 1,3-dimethylbutyl amine, 2-ethylhexylamine, 1-cyclopentyl-2-amino propane, 1,1,3-tetramethylbutylamine, ethylene diamine, methylene diamines, ethanolamine, octylamines, n-decylamine, do-, tetra-, hexa-, octa-, dido-, ditetra-, diocta-, trido- and triocta- decyl amines, aniline, chloroanilines, nitroanilines, toluidines, naphthylamines, N-methyl and N-ethyl, and N,N-dimethyl and N,N-diethyl aniline, di- and triphenylamines, N,N-diamylaniline, benzyl dimethyl amine, piperidine, pyrrolidine, etc. The preferred amines are ammonia and the tertiary amines such as triethylamine.

The metal salt catalysts which may be employed in the process of this invention are the palladium, platinum, rhodium, copper, cobalt, cadmium and zinc salts. Among the chemical forms of the metal compounds which can be used are the palladium, platinum and rhodium, halides, sulfates, oxalates and acetates and the copper halides preferably the palladium (I) and copper (I) or (II) halides such as palladium (II) chloride, palladium (II) iodide, copper (II) chloride and copper (I) iodide. Representative catalytic metal salt compounds include, for example, palladium (II) chloride, copper (II) chloride, rhodium (II) chloride, copper (II) iodide, palladium (II) sulfate, palladium (II) oxalate, palladium (II) acetate, palladium (II) iodide, rhodium (III) bromide, platinum (II) chloride, platinum (II) sulfate, cobalt (II) chloride, cadmium chloride, zinc chloride, etc.

The catalysts employed may be in a homogeneous state in the reaction mixture at reaction conditions. Thus, the catalysts may be present in solution, or suspension and may also be on support materials such as alumina, silica gel, aluminosilicates, activated carbon or zeolites.

The reaction is generally carried out in the presence of a catalytic proportion of the metal salt catalyst and will proceed with small amounts of the metal salt catalyst compounds herein above described. Generally the proportions of the metal salt catalyst used in the reaction will be equivalent to between about 0.001 to 5 weight percent of the acetal or ketal employed and are preferably employed in amounts between about 0.01 to 2 percent by weight of the acetal or ketal employed. Larger or smaller amounts may be employed at varied pressures and temperatures.

As mentioned hereinabove, a ligand or coordination complex compound of the metal catalyst may be employed in the process of the invention as a cocatalyst and thereby also achieve a pronounced increase in the selectivity for the oxalate ester. The ligands may be, for example, alkyl or aryl phosphines, arsines, iodides or stibines. The complexes of the metal catalysts which are suitable as co-catalysts in the process of the present invention include complex compounds of palladium, platinum, rhodium cadmium, cobalt, zinc and copper. The complex compounds may contain one or more atoms of the said metals in the molecule and when more than one such atom is present, the metals may be the same or different. The mono- or poly-dentate ligands which are present in the molecule of the complex compounds and in which at least one of the electron-donating atoms is an atom of phosphorous, arsenic or antimony or an iodide ion containing a lone pair of electrons may be, for example, organo-phosphines, -iodides, -arsines and -stibines. Suitable mono-dentate ligands include alkyl phosphines such as trimethylphosphine and tributylphosphine, aryl-phosphines such as diethylphenyl-phosphine and radicals derived from such phosphines, for example the radical having the formula —P(CH$_3$)$_2$. Hydrocarbyloxy phosphines, i.e., phosphites, such as triphenyl phosphite may also be employed. Suitable polydentate ligands include tetramethyl diphosphinoethane and tetraphenyl diphosphinoethane. Exactly analogous derivatives of arsenic and antimony may be used; however, because of their greater ease of preparation and stability of the derived complexes, the hydrocarbyl derivatives of phosphorus are preferred. If is also preferred to employ alkaline metal iodides, e.g. lithium iodide.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and SnCl$_3$— groups; molecules which may be bonded to the metal include, for example organic isocyanides and isothiocyanates.

Examples of suitable complex compounds are those represented by the following formulae:

RhBr$_3$(PPhEt$_2$)$_3$      Rh(CO)Cl(AsEt$_3$)$_2$
RhCl(CO)(PPhEt$_2$)$_2$      RhCl(CO)(PEt$_3$)$_2$
Rh(Ph$_2$PCH$_2$CH$_2$PPh$_2$)$_2$Cl      PdCl$_2$(PPh$_3$)$_2$
RhI(PhO)$_3$P]$_3$Cl
PdI$_2$(PPh$_3$)$_2$      Li$_2$PdI$_4$

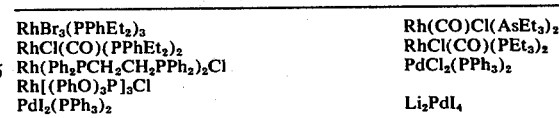

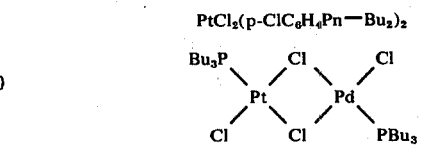

The complex compounds employed may be introduced into the reaction mixture in such, or they may be formed in situ from a suitable metal compound noted above and the desired ligand.

The ligand or complex compounds may be used in catalytic amounts of from 0 to 3 percent preferably from 0.1 to 1 percent by weight of the acetal or ketal to be reacted although larger or smaller amounts may be employed at varied pressures or reaction rates.

The oxidizing salts which may be employed in an anhydrous condition and in catalytic amounts of from 0 to 10 weight percent preferably 3 to 5 weight percent in the process of the invention include the copper (II) salts such as the sulfates, trifluoroacetates, oxalates, or acetates preferably the copper (II) sulfates and trifluoroacetates. Representative oxidant salts include, for example, copper (II) sulfate, copper (II) trifluoroacetate, copper (II) acetate, copper (II) oxalate, copper (II) triflate and copper (II) flurosulfonate. Excess chlorides are detrimental to the reaction system of the present invention.

The amine salts which are employed in an anhydrous condition and in a catalytic amount of from 0 to 10 weight percent preferably in a concentration ~10 weight percent in the process of the invention include, for example, the ammonium and substituted ammonium sulfates, trifluoroacetates, and acetates, preferably the tertiary amine sulfates such as triethyl ammonium sulfate. Representative amine salts include, for example diethylammonium sulfate, ethylammonium sulfate, butylammonium sulfate, ammonium sulfate, trimethylammonium sulfate, mono-methylammonium sulfate, trimethyl ammonium hydrogen sulfate, ammonium acetate, ammonium trifluoroacetate, methyl-, ethyl- and butylammonium trifluoroacetate, etc.

The amine salts may be added as such or formed in situ in the required amounts upon the addition of an acid, such as, sulfuric, benzene sulfonic, phosphoric, o-boric, p-toluene sulfonic, acetic or trifluoroacetic, to the reaction mixture while using greater than the required quantities of the amine base. The acids which may be used to form the salt include those which do not form a complex with the metal salt catalyst or when employed the metal salt oxidant compounds inactivating the catalyst and oxidant. As indicated hereinabove the acids must be of sufficient strenght, i.e., stronger than water, and such that the anion will not complex with the metal catalyst or oxidant salt. The salts which may be formed in situ may in themselves not necessarily be isolable and may exist in equilbrium in the reaction mixture under carbonylation rection conditions. Thus, such salts could not be added per se but, as indicated above may be formed in situ upon the addition of a suitable acid to the reaction mixture containing amine.

Although not required, solvents, if desired, which are chemically inert to the components of the reaction system may be employed. Suitable solvents include, for example, organic esters such as ethyl acetate, n-propyl formate, isopropyl acetate, sec- and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, acetone, cyclohexanone, methyl formate, etc.

As indicated above the reaction can be suitably performed by introducing the oxygen and carbon monoxide at a desired pressure into contact with the acetal or ketal reaction medium containing the specified reactants, catalyst, alcohol and amine and preferably an amine salt and oxidant salt and heating to the desired temperature. In general, a carbon monoxide pressure of about 500 psi to about 3000 psi partial pressure and preferably from 900 psi to about 2200 psi is employed. Stoichiometric quantities of carbon monoxide are generally employed. However, an excess of carbon monoxide may be employed, for example, in continuous processes where a large excess of or high carbon monoxide requirements are generally utilized, a suitable recycle of the carbon monoxide may be employed. The reaction will proceed at temperatures of from about 50° C. to 200° C. It is generally preferred to operate the process at temperatures in the range of 100° C. to 135° C. to obtain a convenient rate of reaction. Heating and/or cooling means may be employed interior and/or exterior of the reaction to maintain the temperature within the desired range.

At least stoichiometric amounts of oxygen or an oxygen containing gas such as air are generally employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent.

The reaction time is generally dependent upon the acetal or ketal being reacted, temperature, pressure and on the amount and type of catalyst being charged as well as the type of equipment being employed. Reaction times will vary dependent on whether the process is continuous or batch.

The following examples are provided to illustrate the invention in accordance with the principles of this invention but are not to be construed as limiting the invention in any way except as indicated by the appended claims.

In the Examples which follow the reactions were run in a 300 ml stainless steel stirred autoclave. The liquid and solid materials were charged to the reactor (as solutions whenever possible). At least 500 psi CO was charged to the reactor, which was heated to reaction temperature. The pressure was increased to the desired value by adding more CO. Oxygen was added in such an amount that a potentially explosive gas mixture was never obtained in the reactor. Enough CO was employed to sweep the oxygen out of the entire length of the tubing and into the reactor. The ensueing rate of gas uptake was allowed to level off before the next addition of CO or oxygen. Additional CO was charged to maintain constant pressure. When an exotherm was observed, cold water was circulated through the internal cooling coil to maintain the reaction temperature within + 5° C. The process of charging oxygen and sweeping out the line with CO was repeated until no more gas uptake was observed. The reactor was cooled to ambient temperature. A gas sample was obtained, and the composition was determined by mass spectral analysis. The liquid product was analyzed by gas-liquid phase chromatography for the oxalate and carbonate ester.

EXAMPLE I

The following materials were charged to the autoclave: a solution of 2.34 g. triethylamine (23.0 mmoles), 3.0 g. methanol (93.6 mmoles), and 70 ml. cyclohexanone dimethyl ketal (0.46 mole) and the solids, 0.25 g. palladium (II) iodide, 6.96 g. triethylammonium sulfate, and 3.70 g. anhydrous copper (II)

sulfate. The reaction temperature was 100° C. The total initial pressure at reaction temperature was 1500 psi. 100 psi oxygen was added followed by 300 psi CO. An exotherm and pressure drop were observed. Another 100 psi CO charge was added. The oxygen/CO charge cycle was repeated six more times using 200–300 psi CO to chase in each 100 psi oxygen charge. The results were the same. A total of 1630 psi pressure drop was observed during a reaction time of approximately 4.8 hours. The total pressure ranged between 1500 and 2110 psi during the reaction. The reaction was not allowed to run to completion. Unreacted ketal and cyclohexanone were detected in the liquid reaction product. 37.8 g. dimethyl oxalate (0.32 mole) and 1.80 g. dimethyl carbonate (0.02 mole) were obtained. 7.26 g. $CO_2$ (0.165 mole) was detected in the gaseous product.

EXAMPLE II

The following materials were charged to the autoclave: a solution of 0.19 g. lithium iodide (1.41 mmoles), 2.34 g. triethylamine (23.0 mmoles), 6.96 g. triethylammonium sulfate (23.0 mmoles), 50 ml n-butanol (0.546 mole), and 61.7 g. of a mixture of 70.6 weight percent cyclohexanone di-n-butyl ketal (0.191 mole), 8.4 weight percent cyclohexanone, and 19.6 weight percent n-butanol (0.163 mole). The charged solids were 0.25 g. palladium (II) iodide (0.69 mmole) and 3.70 g. anhydrous copper (II) sulfate (23.0 mmoles). The reaction temperature was 100° C. The initial pressure at reaction temperature was 1500 psi. 100 psi oxygen was charged followed by 200 psi CO. An exotherm and pressure drop were noted. The oxygen/CO cycle was repeated seven more times. A total of 1870 psi pressure drop was observed during a reaction time of approximately 4.1 hours. The total pressure varied between 1500 and 2190 psi. According to gas-liquid chromatographic analysis, cyclohexanone and n-butanol were present while all of the ketal was consumed. Di-n-butyl oxalate (27.3 g.; 98 percent; 0.132 mole) was isolated by distillation and identified by spectroscopic analysis. Di-n-butyl carbonate was detected in the distillate.

EXAMPLE III

To the autoclave was charged 0.25 g. palladium (II) iodide (0.69 mmole), 3.70 g. anhydrous copper (II) sulfate (23.0 mmoles), and a solution of 0.19 g. lithium iodide (1.41 mmoles), 2.34 g. triethylamine (23.0 mmoles), 6.96 g. triethylammonium sulfate (23.0 mmoles), 3.0 g. methanol (93.6 mmoles), and 70 ml 2,2-dimethoxypropane (0.57 mole). The reaction temperature was 100° C. while the initial pressure at this temperature was 1500 psi. 100 psi oxygen was charged followed by 200 psi CO. An exotherm and rapid pressure drop were observed. Another 100 psi CO charge was made in order to maintain the pressure above 1600 psi. The oxygen/CO cycle was repeated seven more times using between 170 and 400 psi CO per 100 psi oxygen charge. The total pressure drop was 2420 psi. The reaction required approximately 5.5 hours to complete. The total pressure ranged between 1500 and 2170 psi during the course of the reaction. According to gas-liquid chromatographic analysis, all of the ketal was consumed; acetone was the major coproduct. The liquid product contained 60.6 g. dimethyl oxalate (0.513 mole) and 1.5 g. dimethyl carbonate (0.017 mole). The gaseous product contained 5.28 g. $CO_2$ (0.120 mole).

EXAMPLE IV

A solution of 0.38 g. lithium iodide (23.0 mmoles), 2.34 g. triethylamine (23.0 mmoles), 6.96 g. triethylammonium sulfate (23.0 mmoles), 3.0 g. methanol (93.6 mmoles), and 70 ml 2,2-dimethoxypropane (0.57 mole) was charged to the high-pressure autoclave along with 0.27 g. copper (I) iodide (1.41 mmoles) and 3.70 g. copper (II) sulfate (23.0 mmoles). The reaction temperature was 125° C. The total initial pressure was 1500 psi. 100 psi oxygen followed by 200 psi CO was charged to the reactor. A relatively small exotherm and a slow pressure drop were noted. Another charged of 50 psi CO gave a small pressure drop. The oxygen/CO charge cycle was repeated four more times using 200–300 psi CO following the oxygen addition. The reaction was carried out to completion. The total pressure drop was 1060 psi. The approximate reaction time was 4.4 hours. The total pressure range during reaction was 1500–2130 psi. Gas-liquid chromatographic analysis showed the presence of unreacted ketal as well as acetone. The reaction product was determined to contain 33.1 g. dimethyl oxalate (0.28 mole) and 2.4 g. dimethyl carbonate (0.027 mole). The gaseous product contained 0.97 g. $CO_2$ (0.022 mole).

EXAMPLE V

The same materials in Example IV were charged to the autoclave in the same amounts along with 0.31 g. hydroquinone (2.82 mmoles). The reaction temperature was 125° C. The total initial pressure at reaction temperature was 1500 psi. 100 psi oxygen was charged followed by 200 psi CO. No exotherm was detected, and the pressure drop was relatively slow (compared with Example IV). When the pressure levelled out, another oxygen/CO charge was made. The exotherm was more pronounced and the pressure drop was more rapid. The oxygen/CO charge cycle was repeated six more times. The reaction was not taken to completion. The total pressure drop was 1500 psi. The pressure range during the reaction was 1500–2075 psi. The reaction time was approximately 6.5 hours. The liquid product analysis showed the presence of acetone and the absence of ketal. 44.9 g. dimethyl oxalate (0.38 mole) and 3.1 g. dimethyl carbonate (0.034 mole) were found in the liquid product. The gaseous product contained 2.4 g. $CO_2$ (0.055 mole).

EXAMPLE VI

A solution of 2.34 g. triethylamine (23.0 mmoles), 3.0 g. methanol (93.6 mmoles), and 70 ml 2,2-dimethoxypropane (0.57 mole) was charged to the autoclave along with 0.20 g. copper (I) bromide (1.41 mmoles, 0.24 g. lithium bromide (2.82 mmoles), 6.96 g. triethylammonium sulfate (23.0 mmoles), and 3.70 g. anhydrous copper (II) sulfate (23.0 mmoles). The reaction temperature was 125° C. The total initial pressure at temperature was 1500 psi. The first addition of 100 psi oxygen followed by 200 psi CO resulted in a relatively slow pressure drop without any detectible exotherm. Oxygen/CO charge cycle was repeated a total of five more times. The pressure range during the reaction was 1500–2190 psi. Approximate reaction time was 4.1 hours. The total pressure drop was 710 psi. Unreacted ketal was detected in the liquid reaction product as well as acetone. Glc analysis showed the pressure of 11.3 g. dimethyl oxalate (0.096 mole) and 9.55 g. dimethyl carbonate (0.106 mole). Mass spectral analysis of the gas showed the presence of 2.0 g. $CO_2$ (0.045 mole).

EXAMPLE VII

To the autoclave was charged a solution of 2.34 g. triethylamine (23.0 mmoles), 6.96 triethylammonium sulfate (23.0 mmoles), 1.0 g. methanol (31.2 mmoles), 40 ml acetone (0.55 mole), and 70 ml 2,2-dimethoxypropane (0.57 mole) in addition to the solids, 0.27 g. copper (I) iodide (1.41 mmoles), 0.38 g. lithium iodide (2.84 mmoles), and 3.70 g. anhydrous copper (II) sulfate (23.0 mmoles). The reaction temperature was 125° C. The total initial pressure was 1500 psi at reaction temperature. 100 psi oxygen followed by 200 psi CO was charged to the autoclave. No gas uptake was observed. A second oxygen/CO charge was added. A pressure drop was observed. The oxygen/CO charge was repeated four more times. [The reactor had to be cooled to ambient temperature and the gases had to be vented once during this run because the pressure in the reactor became too high to be handled safely. The reaction was continued after reheating to 125° C. and repressuing to 1500 psi with CO.] The reaction was not necessarily taken to completion. The total pressure drop was 800 psi during a reaction period of 3.3 hours. The total pressure ranged between 1650 and 2100 psi during the course of the reaction. Glc analysis of the liquid product showed the presence of unreacted ketal in addition to methanol, a trace of dimethyl carbonate, and 13.9 g. dimethyl oxalate (0.118 mole). The gaseous reaction products contained 0.82 g. $CO_2$ (0.019 mole).

EXAMPLE VIII

A solution of 2.34 g. triethylamine (23.0 mmoles), 3.0 g. methanol (94 mmoles) and 70 ml. dimethoxymethane (0.817 mole) was charged to the autoclave in addition to 0.25 g. palladium (II) iodide (0.69 mmole), 0.19 g. lithium iodide (1.41 mmoles), 3.70 g. copper (II) sulfate (23 mmoles) and 0.50 g. boric acid (8.1 mmoles). The reaction temperature was 125° C. The total initial pressure at reaction temperature was 1500 psi. 200 psi oxygen was charged followed by 400 psi CO. A relatively small pressure drop (130 psi) was observed over a period of 1.8 hours. The reaction was interrupted at this point, and the reaction product was analyzed. The liquid product contained a large amount of unreacted acetal, dimethyl oxalate, dimethyl carbonate (trace), and methanol. $CO_2$ was detected in the gaseous product.

EXAMPLE IX

A solution of 7.02 g. triethylamine (69.4 mmoles), 3.04 g. 96.7 percent sulfuric acid (30.0 mmoles), 3.0 g. ethanol (65.1 mmoles), and 70 ml 1,1-diethoxyethane (0.492 mole) is charged to the autoclave along with 0.25 g. palladium (II) sulfate (1.23 mmoles), 0.20 g. potassium iodide (1.23 mmoles) and 3.70 g. copper (II) sulfate (23.0 mmoles). The reaction temperature is 100° C. The procedure of Example VIII is repeated. The liquid reaction product is found to contain unreacted acetal and ethanol in addition to acetaldehyde, diethyl oxalate, and a trace amount of diethyl carbonate (according to glc analysis). $CO_2$ was detected in the gaseous product.

I claim:

1. A process for the preparation of oxalate esters which comprises reacting under substantially anhydrous conditions, an acetal having the formula

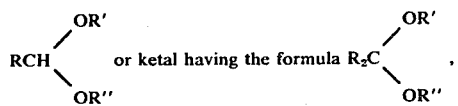

wherein R may be an alkyl, aryl or alicyclic group R' and R" may be an alkyl or aralkyl group which may contain substituents which do not interfere with the reaction, with carbon monoxide and oxygen at a pressure of between about 500 psi and 3000 psi and at a temperature in the range of about 50° C. to 200° C. in the presence of an effective amount of a catalyst selected from the group consisting of palladium, platinum, rhodium, cadmium, cobalt, zinc and copper salt compounds and a catalytic amount of an aliphatic, cycloaliphatic, aromatic or heterocyclic amine or ammonia and a monohydric aliphatic, alicyclic or aromatic alcohol and recovering the desired oxalate ester.

2. A process according to claim 1 wherein the reaction is carried out in the presence of a catalytic amount of a copper (II) or iron (III) oxidant salt compound and an acid or an ammonium or substituted ammonium salt compound.

3. A process according to claim 2 wherein the oxidant salt compound is copper (II) or iron (III) oxalate, sulfate, acetate or trifluoroacetate.

4. A process according to claim 3 wherein the oxidant salt compound is copper (II) sulfate.

5. A process according to claim 2 wherein the ammonium salt compound is triethyl ammonium sulfate.

6. A process according to claim 1 wherein the catalyst salt compound is selected from the group consisting of palladium, platinum, rhodium, cadmium, cobalt, and zinc, halides, oxalates, sulfates and acetates and copper halides.

7. A process according to claim 6 wherein the catalyst is selected from palladium chloride, palladium iodide, copper iodide and copper bromide.

8. A process according to claim 7 wherein the catalyst is palladium iodide.

9. A process according to claim 7 wherein the catalyst is copper iodide.

10. A process according to claim 1 wherein the amine is employed in concentration of from 0.1 to 5 weight percent.

11. A process according to claim 10 wherein the amine is triethylamine.

12. A process according to claim 1 wherein the alcohol is employed in concentrations of from 0.1 to 50 weight percent 13. A process according to claim 1 wherein the alcohol is selected from the group consisting of methyl alcohol, ethyl alcohol, isopropyl alcohol and butyl alcohol.

14. A process according to claim 13 wherein the alcohol is methyl alcohol.

15. A process according to claim 1 wherein the reaction is carried out in the presence of a cocatalytic amount of an organic mono- or poly-dentate ligand selected from the group consisting of alkyl, aryl and halogen substituted phosphines, arsines, stibines and iodides.

16. A process according to claim 15 wherein the ligand is lithium iodide.

17. A process according to claim 1 wherein the pressure is between about 900 psi and 2200 psi and the temperature is in the range of about 100° C. to 135° C.

18. A process according to claim 2 wherein the ammonium or substituted ammonium salt compound is formed in situ upon the addition of an acid.

19. A process according to claim 18 wherein said acid is sulfuric acid.

20. A process for the preparation of oxalate esters which comprises reacting under substantially anhydrous conditions an acetal having the formula

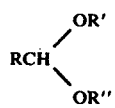

wherein R may be an alkyl, aryl or alicyclic group and R' and R'' may be an alkyl or aralkyl group which may contain substituents which do not interfere with the reaction, with carbon monoxide and oxygen at a pressure of between about 900 psi and 2200 psi and at a temperature in the range of about 100° C. to 135° C. in the presence of an effective amount of a catalyst selected from the group consisting of palladium, platinum, rhodium, cadmium, cobalt, zinc and copper salt compounds, a catalytic amount of an aliphatic, cycloaliphatic, aromatic or heterocyclic amine or ammonia, and a catalytic amount of a monohydric saturated aliphatic, alicyclic or aromatic alcohol and recovering the desired oxalate.

21. A process according to claim 20 wherein the reaction is carried out in the presence of a catalytic amount, of a copper (II) or iron (III) oxidant salt compound, an acid or an ammonium or substituted ammonium salt compound and an organic mono- or polydentate ligand or iodide.

22. A process for the preparation of oxalate esters which comprises reacting under substantially anhydrous conditions a ketal having the formula

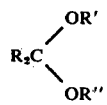

wherein R may be an alkyl, aryl or alicyclic group and R' and R'' may be an alkyl or aralkyl group which may contain substituents which do not interfere with the reaction, with carbon monoxide and oxygen at a pressure of between about 900 psi and 2200 psi and at a temperature in the range of about 100° C. to 135° C. in the presence of an effective amount of a catalyst selected from the group consisting of palladium, platinum, rhodium, cadmium, cobalt, zinc and copper salt compounds, a catalytic amount of an aliphatic, cycloaliphatic, aromatic or heterocyclic amine or ammonia, and a catalytic amount of a monohydric saturated aliphatic, alicyclic or aromatic alcohol and recovering the desired oxalate.

23. A process according to claim 22 wherein the reaction is carried out in the presence of a catalytic amount, of a copper (II) or iron (III) oxidant salt compound, an acid or an ammonium or substituted ammonium salt compound and an organic mono- or polydentate ligand or iodide.

24. A process according to claim 1 wherein an oxygen-containing gas is employed as a source of oxygen for the reaction.

25. A process according to claim 1 wherein the catalyst is supported.

* * * * *